US009034918B2

(12) United States Patent
Tesse

(10) Patent No.: US 9,034,918 B2
(45) Date of Patent: May 19, 2015

(54) COMPOSITION INCLUDING AT LEAST ONE TRANS-CINNAMALDEHYDE AND THE USE THEREOF IN THE TREATMENT OF BACTERIAL INFECTIONS, SPECIFICALLY IN THE TREATMENT OF NOSOCOMIAL INFECTIONS

(75) Inventor: Nicolas Tesse, Vaucresson (FR)

(73) Assignee: SEPTEOS, Paris (FR)

( * ) Notice: Subject to any disclaimer, the term of this patent is extended or adjusted under 35 U.S.C. 154(b) by 553 days.

(21) Appl. No.: 13/376,317

(22) PCT Filed: Jun. 7, 2010

(86) PCT No.: PCT/EP2010/057905
§ 371 (c)(1),
(2), (4) Date: Dec. 5, 2011

(87) PCT Pub. No.: WO2010/139805
PCT Pub. Date: Dec. 9, 2010

(65) Prior Publication Data
US 2012/0077875 A1 Mar. 29, 2012

(30) Foreign Application Priority Data
Jun. 5, 2009 (FR) ...................................... 09 53734

(51) Int. Cl.
| | |
|---|---|
| *A01N 43/16* | (2006.01) |
| *A01N 37/10* | (2006.01) |
| *A01N 35/00* | (2006.01) |
| *A61K 9/00* | (2006.01) |
| *A61K 31/015* | (2006.01) |
| *A61K 31/045* | (2006.01) |
| *A61K 31/08* | (2006.01) |
| *A61K 31/11* | (2006.01) |
| *A61K 31/22* | (2006.01) |
| *A61K 31/352* | (2006.01) |
| *A61K 31/37* | (2006.01) |
| *A61K 45/06* | (2006.01) |
| *A61L 29/16* | (2006.01) |

(52) U.S. Cl.
CPC ............ *A61K 9/0014* (2013.01); *A61K 31/015* (2013.01); *A61K 31/045* (2013.01); *A61K 31/08* (2013.01); *A61K 31/11* (2013.01); *A61K 31/22* (2013.01); *A61K 31/352* (2013.01); *A61K 31/37* (2013.01); *A61K 45/06* (2013.01); *A61L 29/16* (2013.01); *A61L 2300/216* (2013.01); *A61L 2300/404* (2013.01); *A61L 2300/45* (2013.01)

(58) Field of Classification Search
CPC ... A61K 31/045; A61K 31/11; A61K 31/352; A61L 2300/216
USPC .......................... 514/456, 544, 546, 699, 701
See application file for complete search history.

(56) References Cited

U.S. PATENT DOCUMENTS

| 4,477,361 A | 10/1984 | Sperti et al. |
| 2008/0131533 A1 | 6/2008 | Kvitnitsky et al. |

FOREIGN PATENT DOCUMENTS

| WO | WO 01/07094 A1 | 2/2001 |
| WO | WO 2007/109804 A2 | 9/2007 |

OTHER PUBLICATIONS

Paranagama et al.,J. Natn. Sci. Foundation Sri Lanka, 2001;29(3 &4):147-153.*
Chaudhry et al., Pak. J. Bot., 2006;38(1):169-174.*
Ooi et al., The American Journal of Chinese Medicine, 2006:34(3):511-522.*
Ali et al., "Chemical Composition and Antimicrobial Activities of the Essential Oils of *Cinnamomum aureofulvum* Gamb", Journal of Essential Oil Research, vol. 14 (2002) pp. 135-138.
Chang et al., "Antibacterial activity of leaf essential oils and their constituents from *Cinnamomum osmophloeum*", Journal of Ethnopharmacology, vol. 77 (2001) pp. 123-127.
Database WPI, Week 200277, Thomson Scientific, London (GB), XP002593857, (English language abstract of JP 2002-256300 (2002)).
de Billerbeck, "Huiles essentielles et bacteries resistantes aux antibiotiques", Phytotherapie, vol. 5 (2007) pp. 249-253., with English language abstract.
Ezzaouia et al., "Investigation of essential oils to fight multiresistant bacteria in hygienic and therapeutic applications", International Journal of Essential Oil Therapeutics, vol. 1, No. (2008) pp. 51-55.
Lee et al., "Antifungal property of the essential oils and their constituents from *Cinnamomum osmophloeum* leaf against tree pathogenic fungi", Journal of the Science of Food and Agriculture, vol. 85 (2005) pp. 2047-2053.
Mayaud et al., "Comparison of bacteriostatic and bactericidal activity of 13 essential oils against strains with varying sensitivity to antibiotics", Letters in Applied Microbiology, vol. 47 (2008) pp. 167-173.
Rattanachaikunsopon et al., "Potential of cinnamon (*Cinnamomum verum*) oil to control *Streptococcus iniae* infection in tilapia (*Oreochromis niloticus*)", Fish Science, vol. 76 (2010) pp. 287-293.
Sacchetti et al., "Essential oil of wild *Ocotea quixos* (Lam.) Kosterm. (Lauraceae) leaves from Amazonian Ecuador", Flavour and Fragrance Journal, vol. 21 (2006) pp. 674-676.

(Continued)

*Primary Examiner* — San-Ming Hui
(74) *Attorney, Agent, or Firm* — Birch, Stewart, Kolasch & Birch, LLP

(57) ABSTRACT

The present invention relates to a composition, in particular an antibacterial drug, including trans-cinnamaldehyde, a pharmaceutical composition including trans-cinnamaldehyde for treatment or prevention, in particular, of a nosocomial infection, specifically caused by a bacteria resistant to anti-bacterial drugs, the use of trans-cinnamaldehyde as an anti-bacterial agent and a method for preparing a surface including the application of a composition according to the invention.

29 Claims, No Drawings

(56) References Cited

OTHER PUBLICATIONS

Senhaji et al., "Inactivation of *Escherichia coli* O157:H7 by Essential Oil from *Cinnamomum zeylanicum*", Brazillian Journal of Infectious Diseases, vol. 11, No. 2 (2007) pp. 234-236.

Shahverdi et al., "Trans-Cinnamldehyde from *Cinnamomum zeylanicum* Bark Essential Oil Reduces the Clindamycin Resistance of *Clostridium difficile* in vitro", J. of Food Science, vol. 72, No. 1 (2007) pp. S55-S58.

* cited by examiner

COMPOSITION INCLUDING AT LEAST ONE TRANS-CINNAMALDEHYDE AND THE USE THEREOF IN THE TREATMENT OF BACTERIAL INFECTIONS, SPECIFICALLY IN THE TREATMENT OF NOSOCOMIAL INFECTIONS

The present invention relates to the field of antibacterial drugs. More precisely, it relates to a composition, in particular an antibacterial or pharmaceutical composition, notably used in the context of the treatment of bacterial infections, particularly those induced by resistant bacteria, in particular in a hospital environment.

The arrival of penicillin and then streptomycin in the 1940's opened the era of antibacterial drugs. The introduction of penicillin, followed by many other antimicrobial agents such as aminoglycosides, beta-lactams, macrolides and quinolones, represented one of greatest successes of modern medicine in the treatment of bacterial infections.

However, the need for novel molecules to fight bacterial infections is growing. Indeed, in human health in particular, nosocomial infections are serious infections which affect hospitalized patients. They prove particularly dangerous for patients whose immune system is weakened, for example following treatments such as corticosteroid therapy or chemotherapy, procedures such as transplantations or diseases affecting the immune system such as acquired immune deficiency syndrome (AIDS). The increase in the frequency and severity of nosocomial infections coincides with the emergence of bacteria that are resistant to existing antibacterial drugs.

As examples of Gram-positive bacteria exhibiting a phenomenon of pharmacoresistance, particular mention may be made of bacteria of the genus *Staphylococcus*, in particular *Staphylococcus aureus*, and bacteria of the genus *Enterococcus*, in particular *Enterococcus faecalis*.

As examples of Gram-negative bacteria exhibiting a phenomenon of pharmacoresistance, particular mention may be made of bacteria of the genus *Escherichia*, in particular *Escherichia coli*, bacteria of the genus *Pseudomonas*, in particular *Pseudomonas aeruginosa*, and bacteria of the genus *Acinetobacter*, in particular *Acinetobacter baumannii*.

A worrying example is that of *Staphylococcus aureus*. Indeed, more than 95% of *Staphylococcus aureus* bacterial strains are resistant to penicillin and more than 60% have also become resistant to its derivative, methicillin. Strains with reduced sensitivity to vancomycin have also been characterized.

According to the World Health Organization, the percentage of methicillin-resistant *Staphylococcus aureus* strains that have become resistant to mipirocin, an antibacterial that inhibits protein synthesis, increased by 2.7% to 65% in the space of three years. This shows that the action of conventional antibacterial analogues may be quickly countered by mechanisms of multiple resistances developed by bacteria.

The phenomenon of pharmacoresistance is all the more worrying as it is no longer confined to hospitals but now tends to be distributed throughout the community. Indeed, a high prevalence of infections caused by *Staphylococcus aureus* in persons of 65 years of age and older is observed. The incidence of bacterial infections, pneumonia, endocarditis and osteoarticular or urinary bacterial infections developed by the elderly and linked to *Staphylococcus aureus* is particularly worrying.

Gram-negative bacilli, in particular enterobacteria and *Pseudomonas aeruginosa*, are naturally resistant, most often at a low level, to hydrophobic and/or high molecular weight antibacterials (penicillin G, penicillin M, macrolides, rifampicin, fusidic acid, novobiocin, vancomycin) because these antibacterials cannot cross the external membrane of the bacterial cell wall.

The appearance and propagation of bacterial strains resistant to practically all currently available antimicrobial agents has become a major health problem.

There is thus a growing need to characterize and obtain novel classes of antibacterial molecules, more particularly active against Gram-positive bacteria and/or Gram-negative bacteria, if possible active against both Gram-positive bacteria and Gram-negative bacteria.

One of the goals of the invention is thus to obtain antibacterial agents active against a broad spectrum of bacteria, in particular against resistant strains. According to one variant, said bacterial agents are active on strains exhibiting non-natural resistance. According to another variant, said bacterial agents are active on strains exhibiting natural resistance.

The definition of natural resistance may be found in particular on pages 15, 16 and 17 of Communiqué 2006 (edition of January 2006) of the Antibiogram Committee of the French Microbiology Society.

In infectious pathology, a bacterium is referred to as "resistant" when the concentration of antibacterial that it is able to tolerate is notably higher than that which is possible to obtain in vivo following a treatment.

One of the goals of the invention is also to identify antibacterial agents that exhibit strong activity, in particular at a low dose, with respect to their targets.

Among the other goals of the invention, mention may be made of the obtaining of antibacterial agents that are relatively inexpensive, that are easy to prepare, that exhibit a broad or even very broad spectrum of activity, that exhibit antifungal activity, that are active even in the presence of interfering agents, that trigger no or little resistance, in particular cross-resistance, and/or that are well tolerated in and/or on the organism to be treated.

The Inventors discovered, in an unexpected manner, that these goals could be reached, in whole or part, by using a composition including trans-cinnamic aldehyde, also called trans-cinnamaldehyde.

Trans-cinnamic aldehyde or trans-cinnamaldehyde (CAS 14371-10-9) has the following chemical formula:

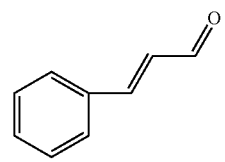

It may include non-negligible quantities, up to a racemic ratio, of its cis-cinnamic aldehyde isomer.

However, trans-cinnamic aldehyde may include less than 20% by weight, in particular less than 10% by weight, in particular less than 5% by weight, or even less than 2% by weight, particularly less than 1% by weight of cis-cinnamaldehyde, or even be free of cis-cinnamaldehyde.

Thus, according to a first aspect, the invention has as an object an antibacterial composition including, or even consisting of, trans-cinnamic aldehyde.

Said antibacterial composition may include, or even consist of, trans-cinnamaldehyde and at least one compound selected from trans-2-methoxycinnamaldehyde, cinnamyl acetate, coumarin, linalool, beta-caryophyllene, eugenol, cineole, benzyl benzoate and safrole, or at least one compound selected from trans-2-methoxycinnamaldehyde, cinnamyl acetate, coumarin, linalool and beta-caryophyllene.

More particularly, the antibacterial composition includes, or even consists of, at least two, in particular at least three, or even at least four, and even more particularly at least five of the compounds mentioned above.

According to a particular embodiment, the antibacterial composition includes, or consists of, at least three different components each chosen from one of the following three groups, respectively:
 trans-cinnamaldehyde,
 at least one compound selected from cinnamyl acetate, trans-2-methoxycinnamaldehyde, eugenol and coumarin, in particular cinnamyl acetate, and
 at least one compound selected from benzyl benzoate, trans-2-methoxycinnamaldehyde, coumarin, eugenol, safrole, beta-caryophyllene, linalool and cineole, in particular benzyl benzoate, safrole, beta-caryophyllene, linalool and cineole.

In particular, said antibacterial composition includes, or even consists of, trans-cinnamaldehyde, at least one compound selected from trans-2-methoxycinnamaldehyde, cinnamyl acetate and coumarin, and at least one compound selected from linalool, cineole, safrole and beta-caryophyllene.

According to another particular embodiment, the antibacterial composition includes at least three different components each chosen from one of the following three groups, respectively:
 trans-cinnamaldehyde,
 cinnamyl acetate, and
 at least one compound selected from linalool in a proportion ranging from 0.25% to 5% by weight in relation to the total weight of the composition, benzyl benzoate, safrole, beta-caryophyllene and cineole.

According to a first specific embodiment, the antibacterial composition consists of at least three different components each chosen from one of the three groups above, respectively.

According to still another particular embodiment, the antibacterial composition includes at least three different components each chosen from one of the following three groups, respectively:
 trans-cinnamaldehyde,
 trans-2-methoxycinnamaldehyde in a proportion ranging from 1% to 10% by weight in relation to the total weight of the composition, and
 at least one compound selected from benzyl benzoate, safrole, beta-caryophyllene, linalool and cineole.

According to a second specific embodiment, the antibacterial composition consists of at least three different components each chosen from one of the three groups above, respectively.

Trans-cinnamaldehyde is present in the composition in a proportion ranging from 30% to 100% by weight, in particular from 40% to 90% by weight, in particular from 50% to 85% by weight, or even from 55% to 80% by weight in relation to the total weight of the composition.

Trans-2-methoxycinnamaldehyde may be present in a proportion ranging from 0.5% to 15% by weight, in particular from 1% to 10% by weight, in particular from 1.5% to 8% by weight, or even from 2.5% to 7.5% by weight in relation to the total weight of the composition.

Cinnamyl acetate may be present in a proportion ranging from 0.1% to 8% by weight, in particular from 0.25% to 5% by weight and in particular from 0.5% to 3% by weight in relation to the total weight of the composition.

Coumarin may be present in a proportion ranging from 0.25% to 5% by weight, in particular from 0.5% to 3.5% by weight and in particular from 0.75% to 2.25% by weight in relation to the total weight of the composition.

However, in a particular embodiment, the proportion of coumarin is less than 1% by weight, in particular less than 0.5% by weight, or the composition is even free of coumarin.

Linalool may be present in a proportion ranging from 0.1% to 8% by weight, in particular from 0.25% to 5% by weight and more particularly from 0.5% to 3% by weight in relation to the total weight of the composition.

Cineole may be present in a proportion ranging from 0.1% to 8% by weight, in particular from 0.25% to 5% by weight and more particularly from 0.5% to 3% by weight in relation to the total weight of the composition.

Safrole may be present in a proportion ranging from 0.01% to 5% by weight, in particular from 0.05% to 2% by weight and more particularly from 0.1% to 1% by weight in relation to the total weight of the composition.

However, in a particular embodiment, the proportion of safrole is less than 1% by weight, in particular less than 0.5% by weight, or the composition is even free of safrole.

Beta-caryophyllene may be present in a proportion ranging from 0.1% to 5% by weight, in particular from 0.25% to 3% by weight and more particularly from 0.5% to 2% by weight in relation to the total weight of the composition.

However, in a particular embodiment, the proportion of beta-caryophyllene is less than 1% by weight, in particular less than 0.5% by weight, or the composition is even free of beta-caryophyllene.

Eugenol may be present in a proportion ranging from 0.01% to 15% by weight, in particular from 0.1% to 10% by weight and more particularly from 0.2% to 7.5% by weight in relation to the total weight of the composition.

However, in a particular embodiment, the proportion of eugenol is less than 1% by weight, in particular less than 0.5% by weight, or the composition is even free of eugenol.

Benzyl benzoate may be present in a proportion ranging from 0.01% to 3% by weight, in particular from 0.05% to 2% by weight and more particularly from 0.1% to 1% by weight in relation to the total weight of the composition.

Said antibacterial composition may optionally include one or more additional components.

Advantageously the composition is free of guaiacol.

The antibacterial composition may include, or consist of:
 40% to 90% by weight in relation to the total weight of the composition of trans-cinnamaldehyde,
 0.5% to 15% by weight of trans-2-methoxycinnamaldehyde,
 0.1% to 8% by weight of cinnamyl acetate,
 0.1% to 8% by weight of linalool,
 0.25% to 5% by weight of coumarin, and
 0.1% to 5% by weight of beta-caryophyllene.

The composition according to the invention may include at least one type of essential oil from the bark and/or leaves, in particular the trunk, small branches and/or whole branches of plants of the genus *Cinnamomum*, in particular the cinnamon tree.

According to a particular embodiment, the antibacterial composition includes, or even consists of, essential oil of Chinese cinnamon and/or essential oil of cinnamon bark.

In the context of the present invention, the expression "essential oil" refers to all of the following:
 natural essential oil, i.e., that obtained by extraction (most often by distillation);
 purified essential oil in which some naturally present compounds are removed. Such a purified oil notably may be a rectified oil, i.e., that obtained by extraction (most often by distillation) and then by an additional step (most often a secondary distillation) intended to remove certain naturally present compounds (for example coumarin);

synthetic essential oil, obtained by chemical synthesis, which may contain all or only part of the naturally present compounds.

Chinese cinnamon is also called cinnamon tree: its Latin name is *Cinnamomi cassiae aetheroleum*. According to the European Pharmacopeia, essential oil of Chinese cinnamon is obtained by steam entrainment of the leaves and young branches of *Cinnamomum cassia* Blume (*C. aromaticum* Nees). The principal components are as follows (percentages expressed by weight in relation to the total weight of essential oil):

trans-cinnamic aldehyde: 70% to 90%
cinnamyl acetate: 1% to 6%
eugenol: <0.5%
trans-2-methoxycinnaamaldehyde: 3% to 15%
coumarin: 1.5% to 4%.

Cinnamon bark is also known as Ceylon cinnamon: its Latin name is *Cinnamomi zeylanicii corticis aetheroleum*. According to the European Pharmacopeia, essential oil of Ceylon cinnamon is obtained by steam entrainment of the bark of young *Cinnamomum zeylanicum* Nees saplings. The principal components are as follows (percentages expressed by weight in relation to the total weight of essential oil):

trans-cinnamic aldehyde: 55% to 75%
eugenol: <7.5%
trans-2-methoxycinnamaldehyde: 0.1% to 1%
coumarin: <0.5%
cineole: <3.0%
linalool: 1% to 6%
beta-caryophyllene: 1% to 4%
safrole: <0.5%
benzyl benzoate: <1%.

Essential oils have been used in traditional medicine for more than 3000 years. Throughout history, this use evolved and eventually led at the beginning of the 20$^{th}$ century to the birth of a branch of allopathic phytotherapy, aromatherapy.

Aromatherapy is a traditional and empirical medicine which uses essential oils to treat a disparate group of diseases. Moreover, pharmacognosy recognizes three principal actions of essential oils and their terpenes: anti-infectious, anti-spasmodic and anti-irritant.

Among these essential oils, essential oil of Chinese cinnamon and essential oil of cinnamon bark are described for their many beneficial properties: positivity, anti-infection, antibacterial, general and sexual, respiratory and nervous tonic and stimulant, hyperemia, anesthetic, anticoagulant.

The so-called "antibacterial" activity of these essential oils described up until now is principally disinfecting activity, used to good benefit in the preservation of foodstuffs. This activity is thus centered on the use in the food industry (food preservation) of these essential cinnamon oils, or their principal active component, trans-cinnamic aldehyde. The activities of these oils have been determined by methods that are in general not very reliable and not very reproducible, thus leading to imprecise or even false results.

In particular, no pharmaceutical antibacterial use with a spectrum of activity in particular specific to resistant bacteria and/or anaerobic bacteria of compositions including in particular trans-cinnamic aldehyde has been envisaged to date.

Particularly, the composition according to the invention, in particular an antibacterial or pharmaceutical composition, is free of antibiotics, in particular traditional antibiotics, notably those mentioned in the present text.

According to another of its aspects, the invention also has as an object a composition, in particular a pharmaceutical composition, or a drug, in particular an antibiotic, including, in particular as an antibacterial active ingredient, trans-cinnamic aldehyde or an antibacterial composition such as described above, for the treatment or prevention of a disease, in particular of community or nosocomial origin, in particular caused by a bacterium, particularly an antibacterial-resistant bacterium, in particular those antibacterials used traditionally, for example in an animal, in particular in a mammal, and in particular in a human being.

Particularly, said composition, in particular a pharmaceutical composition, or drug is intended for the treatment or prevention of bacterial infections caused by anaerobic bacteria.

The antibacterial active ingredient may correspond to the antibacterial composition such as described above and thus may in particular include, or consist of, at least three different components each chosen from one of the following groups:

trans-cinnamaldehyde,
at least one compound selected from cinnamyl acetate, trans-2-methoxycinnamaldehyde, eugenol and coumarin, in particular cinnamyl acetate, and
at least one compound selected from benzyl benzoate, trans-2-methoxycinnamaldehyde, coumarin, eugenol, safrole, beta-caryophyllene, linalool and cineole, in particular benzyl benzoate, safrole, beta-caryophyllene, linalool and cineole.

The antibacterial active ingredient may further include, or even consist of, cinnamaldehyde and at least one compound selected from trans-2-methoxycinnamaldehyde, cinnamyl acetate, coumarin, linalool, beta-caryophyllene, eugenol, cineole, benzyl benzoate and safrole, or at least one compound selected from trans-2-methoxycinnamaldehyde, cinnamyl acetate, coumarin, linalool and beta-caryophyllene.

More particularly, the active ingredient includes, or even consists of, at least two, in particular at least three, or even at least four, and even more particularly at least five of the compounds mentioned above.

More particularly, the antibacterial active ingredient includes, or even consists of, trans-cinnamaldehyde, at least one compound selected from trans-2-methoxycinnamaldehyde, cinnamyl acetate and coumarin, and at least one compound selected from linalool and beta-caryophyllene.

More particularly, the antibacterial active ingredient includes, or even consists of, the first or the second specific embodiment of the composition.

The antibacterial active ingredient may further include or consist of essential oil of Chinese cinnamon, essential oil of cinnamon bark or a mixture of said essential oils.

Lastly, the so-called "synthetic" or "purified" compositions according to the invention, i.e., those including a limited number of components, may also exhibit improved activity and decreased toxicities and/or decreased side effects.

Furthermore, the compositions according to the invention may exhibit bactericidal activity in the presence of interfering substances, for example bovine albumin and/or sheep erythrocytes.

According to another of its aspects, the invention also has for object the use of the antibacterial active ingredient or antibacterial composition for the preparation of a drug.

In the context of the present invention, "resistant bacterium," in particular antibacterial-resistant bacterium, refers to a bacterium resistant to at least one traditionally used antibiotic and/or antibacterial, or antibiotic and/or antibacterial family, in particular at least two, in particular at least three, or even at least four traditionally used antibiotics and/or antibacterials, or family of antibiotics and/or antibacterials. The antibiotic and/or antibacterial may be selected from the compounds belonging to the large families listed below.

In the context of the present invention, "multiresistant bacterium" refers to a bacterium that is resistant to several antibiotics and/or antibacterials, in particular to which the species should be sensitive, or is in principle sensitive, in particular the bacterium has at least two non-natural resistances.

According to the present invention, "antibiotic" refers to an antibacterial substance that helps an organism fight a bacterial infection.

According to the present invention, "antibacterial active ingredient" refers to any molecule exhibiting bacteriostatic or bactericidal properties in particular in vitro, for example in a composition, in particular a pharmaceutical, dietary or cosmetic composition, for the disinfection of industrial or breeding facilities, or in vivo, in particular in animals, and more particularly in humans, and/or fungicidal properties, particularly with respect to yeasts.

According to another of its aspects, the invention also has as an object the use of a composition according to the invention as an antibacterial agent or preservative, in particular in a cosmetic, pharmaceutical and/or dietary composition. The proportion of antibacterial agent and/or preservative may be on the same order as, or even identical to, those stated below.

A substance is bacteriostatic when it suspends or decreases the multiplication of bacteria. Experimentally, measurements are made of the minimum inhibitory concentration (MIC), which is the lowest concentration of the substance for which bacterial growth is no longer observed after 18 to 24 hours of contact under conditions favorable to bacterial growth.

A substance is bactericidal when it definitively destroys the vitality of a bacterium. Experimentally, measurements are made of the logarithmic drop in the microbial population. Bactericidal effect is defined as a 3-log drop in the bacterial population. "Bactericidal effect" in the context of the present invention may also be defined as in example 7.

According to an advantageous variant of the invention, the antibacterial active ingredient and/or composition, in particular a pharmaceutical and/or antibacterial composition, is bactericidal.

The antibiotics, which are antibacterials, known and typically used to date belong in particular to the following large families:
  aminoglycosides,
  beta-lactams, such as cephalosporin beta-lactams, penicillin beta-lactams and other beta-lactams (carbapenems, monobactams),
  cyclines (doxycycline, limecycline, metacycline, minocycline, tetracycline, oxtetracycline, tigecycline),
  glycopeptides (teicoplanin, vancomycin) and polypeptides,
  macrolides and macrolide-like compounds (lincosamides, ketolides, streptogramins),
  quinolones, including fluoroquinolones,
  antibacterial peptides, in particular gramicidin,
  phages, and
  others (fusidic acid, noxytiolin, daptomycin, fosfomycin, oxazolidinone, phenicols, polymyxins, rifampicin, etc.).

More and more bacteria have become resistant to one or more of these classes of antibacterials, in particular antibiotics.

The principal antibacterial agents used to date are more active, or are even specific, in relation to either Gram-negative bacteria or Gram-positive bacteria. In particular, the principal antibacterial agents used to date are more active, or are even specific, to Gram-positive bacteria. There is thus a need for antibacterial agents capable of stopping the development of or, advantageously, destroying the vitality of Gram-negative bacteria, and also of Gram-positive bacteria.

However, in a surprising and highly advantageous manner, the compositions according to the invention exhibit antibacterial activities on both Gram-positive bacteria and Gram-negative bacteria. The compositions according to the invention may be effective on such nonresistant and/or resistant bacteria, and even multiresistant bacteria.

In particular, it was noted that the compositions according to the invention are active with respect to resistant Gram-negative bacteria of the genus:
  *Pseudomonas*, and more particularly *P. aeruginosa*,
  *Acinetobacter*, and more particularly *A. baumannii*,
  *Escherichia*, and more particularly *E. coli*,
  *Enterobacter*, and more particularly *E. aerogenes*.

But it was also noted that trans-cinnamic aldehyde and the compositions according to the invention may be active with respect to resistant Gram-positive bacteria, in particular those of the genus:
  *Staphylococcus*, and more particularly *S. aureus*, and/or
  *Enterococcus*, and more particularly *E. faecalis*.

The compositions according to the invention may be active with respect to anaerobic bacteria, in particular those of the genus:
  *Bacteroides*, in particular *B. fragilis* and *B. thetaiotaomicron*,
  *Eggerthella*, in particular *E. lenta*,
  *Peptostreptococcus*, in particular *P. micros, P.* spp., and *P. anaerobius*,
  *Clostridium*, in particular *C. perfringens* and *C. difficile*,
  *Micromonas*.

In a first variant of the invention, the bacterium is of the genus *Pseudomonas*. This bacterium may be resistant. It is characterized by the observation of at least one resistance from the following:
  fluoroquinolone resistance,
  cephalosporin resistance, in particular $1^{st}$, $2^{nd}$ or $3^{rd}$ generation cephalosporins,
  penicillinase production, i.e., resistance to beta-lactam penicillins, notably in the case of hyperproduction of chromosomal cephalosporinase,
  extended-spectrum beta-lactamase (ESBL) production,
  carbapenemase production, in particular VIM-2 carbapenemase,
  porin defect, in particular D2 porin, which may lead to resistance to beta-lactams other than penicillins and cephalosporins,
  aminoglycoside resistance.

In a second variant of the invention, the bacterium is of the genus *Acinetobacter*. This bacterium may be resistant. It may be characterized by the observation of at least one resistance from the following:
  multiresistance,
  Vietnamese extended-spectrum beta-lactamase (VEB-1).

In a third variant of the invention, the bacterium is of the genus *Escherichia*. This bacterium may be resistant. It may be characterized by the observation of at least one resistance from the following:
  fluoroquinolone and quinolone resistance,
  cephalosporin resistance, in particular $1^{st}$, $2^{nd}$ and $3^{rd}$ generation cephalosporins,
  extended-spectrum beta-lactamase (ESBL) production,
  penicillinase production.

In a fourth variant of the invention, the bacterium is of the genus *Staphylococcus*. This bacterium may be resistant. It may be characterized by the observation of at least one resistance from the following:
methicillin resistance,
aminoglycoside resistance, in particular tobramycin/kanamycin resistance: KT phenotype,
fluoroquinolone resistance.

In a fifth variant of the invention, the bacterium is of the genus *Enterococcus*. This bacterium may be resistant. It may be characterized by the observation of at least one resistance from the following:
aminoglycoside resistance,
resistance to macrolides and to macrolide-like compounds.

In a sixth variant of the invention, the bacterium is of the genus *Enterobacter*. This bacterium may be resistant. It may be characterized by the observation of at least one resistance of extended-spectrum beta-lactamase (ESBL) production.

According to a particular embodiment, the invention has as an object a pharmaceutical composition, or a drug, including, or consisting of, an antibacterial composition according to the invention, in particular as an antibacterial active ingredient.

Said pharmaceutical composition, or said drug, may be intended for the treatment or prevention of bacterial infections, notably caused by an antibacterial-resistant bacterium, for example in an animal, in particular in a mammal, and in particular in a human being.

Particularly, it is intended for the treatment or prevention of bacterial infections caused by anaerobic bacteria.

The composition, in particular a pharmaceutical composition, or the drug may be intended for the treatment or prevention of diseases, in particular nosocomial diseases, related to fungal infections, in particular by yeasts, and/or bacterial infections, in particular by resistant bacteria, or even multi-resistant bacteria.

Said diseases may be selected from the group comprised of urinary tract infections, respiratory system infections, digestive system infections, central nervous system infections, skin and soft tissue infections, bone, joint and muscle infections, vascular system infections, septic shock, diabetic foot and eschars.

Such resistant bacteria are encountered more and more frequently, in particular in a hospital environment, and are the cause of numerous nosocomial syndromes. Fighting such bacteria and/or yeasts thus makes it possible to prevent or treat numerous nosocomial syndromes.

According to an advantageous variant of the invention, the composition according to the invention is intended for the treatment or prevention of nosocomial diseases, in particular via yeasts and/or bacteria, in particular by resistant bacteria, or even multiresistant bacteria.

Said diseases may be selected from the group comprised of urinary tract infections, respiratory system infections, digestive system infections, central nervous system infections, skin and soft tissue infections, bone, joint and muscle infections, vascular system infections, septic shock, diabetic foot and eschars.

In the context of the present invention, "nosocomial infection" refers to any microbial, viral and/or fungal infection contracted in a hospital environment, in particular with an appearance of symptoms at least 24 hours, or at least 48 hours, after admission of the patient.

The present invention also relates to the treatment and prevention of syndromes encountered in the context of the following etiologies:
infections that do not cross epithelial barriers, such as infections by inhalation or ingestion,
infections that cross epithelial barriers, such as infections by punctures, cuts, wounds, transplantation, transfusion, infections related to the use of an invasive medical device (prosthesis, stent),
operative, perioperative and postoperative infections,
infections consecutive to burns.

The composition according to the invention may also be intended to treat and/or to prevent the portage of bacteria, in particular golden staph, in the various flora of the patient, in particular the cutaneous flora, oral flora and nasopharyngeal flora.

Diseases induced by the proliferation of bacteria, and more particularly nosocomial diseases, are most often encountered in co-called "sensitive" individuals. The composition according to the invention is thus particularly intended to treat and/or to prevent nosocomial diseases in immunosuppressed or immunodeficient individuals. Such immunosuppressed or immunodeficient individuals may be the elderly (over 65), infants (younger than 12 months), young children (under 4), patients undergoing corticosteroid therapy, transplant patients and AIDS patients.

In the pharmaceutical composition or the drug, it is possible to use, as an antibacterial active ingredient, either trans-cinnamic aldehyde itself, or a composition containing trans-cinnamic aldehyde in combination with at least one compound selected from trans-2-methoxycinnamaldehyde, cinnamyl acetate, coumarin, linalool and beta-caryophyllene, in particular in combination with at least one compound selected from trans-2-methoxycinnamaldehyde, cinnamyl acetate and coumarin, and at least one compound selected from linalool and beta-caryophyllene. The antibacterial active ingredient may also correspond to the antibacterial composition according to the invention.

The trans-cinnamaldehyde may come from essential oil of Chinese cinnamon or essential oil of cinnamon bark, and optionally from a combination of these two essential oils.

The pharmaceutical composition may include, or consist of, the antibacterial composition. In particular, the pharmaceutical composition may include the antibacterial composition as an active ingredient, and in particular as an antibacterial active ingredient.

Thus, the composition according to the invention may include, or even consist of, essential oil of Chinese cinnamon and/or essential oil of cinnamon bark, in a weight ratio ranging from 9:1 to 1:9, in particular ranging from 4:1 to 1:4, particularly ranging from 2:1 to 1:2, or even a ratio of 1:1.

The experimental results show, for essential oil of Chinese cinnamon, antibacterial activity on resistant strains of *Pseudomonas aeruginosa*, *E. coli*, *Staphylococcus aureus* and *Enterococcus* at volume concentrations varying from 0.125% to 1% (v/v). At a lower concentration (0.06%), antibacterial activity is always observed on all the resistant strains tested. At an even lower concentration (0.03%), antibacterial activity is always observed on most of the resistant strains of *Pseudomonas aeruginosa*, *E. coli*, *Staphylococcus aureus*, *Enterococcus faecium*, *Acinetobacter aerogenes* and *Acinetobacter baumannii*.

The experimental results show, for essential oil of cinnamon bark, antibacterial activity on resistant strains of *Pseudomonas aeruginosa*, *Escherichia coli*, *Staphylococcus aureus*, *Acinetobacter aerogenes* and *Enterococcus* with volume concentrations varying from 0.125% to 1% (v/v). At a lower concentration (0.06%), antibacterial activity is always observed on all the resistant strains of *E. coli*, *Staphylococcus aureus* and *Enterococcus*. At an even lower concentration (0.03%), antibacterial activity is observed only on two resistant strains of *Staphylococcus aureus*.

It is thus noted that these two essential oils provide very good results on resistant bacterial strains, sampled in a hospital environment, with the best results being obtained with essential oil of Chinese cinnamon.

An unexpected synergy effect was also noted in particular for the combination of essential oil of Chinese cinnamon and essential oil of cinnamon bark. When such a combination is used (in a 1:1 volume ratio), antibacterial activity is observed on almost all of the strains even at a very low concentration of 0.06% (v/v).

The invention thus also has as an object the use, in synergy, of essential oil of Chinese cinnamon in combination with essential oil of cinnamon bark. The combination may include the two essential oils in any proportion, with a 1:1 weight ratio being preferred.

This is the first time that such a synergy effect between these two oils has been observed. The invention thus extends to any pharmaceutical composition including as an antibacterial active ingredient a combination of essential oil of Chinese cinnamon and essential oil of cinnamon bark, preferably in a volume ratio of 1:1. The pharmaceutical composition, including a combination of essential oil of Chinese cinnamon and essential oil of cinnamon bark, may be used, in the context of the invention, as an antibacterial drug against both the nonresistant bacteria and the resistant bacteria described above. Said bacteria may be Gram-positive bacteria or Gram-negative bacteria, in particular resistant or nonresistant Gram-negative bacteria of the genus:

*Pseudomonas*, and more particularly *Pseudomonas aeruginosa*,
*Acinetobacter*, and more particularly *Acinetobacter baumannii*,
*Escherichia*, and more particularly *Escherichia coli*,
*Enterobacter*, and more particularly *Enterobacter aerogenes*, or resistant or nonresistant Gram-positive bacteria of the genus:

*Staphylococcus*, and more particularly *Staphylococcus aureus*,
*Enterococcus*, and more particularly *Enterococcus faecalis*.

The "synergy" referred to in the present text may in particular be calculated in the following manner:

$$FIC_{index}=(MIC_{A/B}/MIC_A)+(MIC_{B/A}/MIC_B)$$

wherein $FIC_{index}$ is the fractional inhibitory concentration index,
$MIC_A$=MIC of compound A, in particular of antibiotic A, alone,
$MIC_B$=MIC of compound B, in particular of antibiotic B, alone,
$MIC_{A/B}$=MIC of compound A, in particular of antibiotic A, in a mixture of A+B,
$MIC_{B/A}$=MIC of compound B, in particular of antibiotic B, in a mixture of A+B.

This formula makes it possible to determine if there is a synergy effect, an additive effect, an indifferent effect or an antagonistic effect in the following manner, when:

$FIC_{index}$ is less than or equal to 0.5 there is a synergy effect,
$FIC_{index}$ is greater than 0.5 and less than or equal to 1 there is an additive effect,
$FIC_{index}$ is greater than 1 and less than or equal to 2 there is an indifferent effect, and
$FIC_{index}$ is greater than 2 there is an antagonistic effect.

According to another of its aspects, the invention has as an object a composition in which the antibacterial composition is diluted, wherein said diluted composition may comprise from 1% to 90% by weight, in particular from 5% to 75% by weight, in particular from 10% to 50% by weight, in particular from 20% to 50% by weight in relation to the total weight of the diluted composition of the antibacterial composition.

According to a particular embodiment, the composition according to the invention, an antibacterial or pharmaceutical composition or drug, has a proportion of trans-cinnamaldehyde ranging from 0.1% to 6.5% by weight, in particular from 0.2% to 5.5% by weight, in particular from 0.4% to 5% by weight, or even from 0.5% to 4.5% by weight in relation to the total weight of the composition.

Furthermore, the proportion of antibacterial active ingredient, in particular when said antibacterial active ingredient corresponds to the antibacterial composition as defined according to one of the particular embodiments above, and more particularly according to one of the specific embodiments, may range from 0.05% to 7.5% by weight, in particular from 0.1% to 6% by weight, in particular from 0.2% to 5% by weight, or even from 0.5% to 5% by weight, and particularly from 0.75% to 5% by weight in relation to the total weight of the composition.

The composition according to the invention may be intended to be applied on the skin and/or mucosa, on a device intended to come into contact with the skin and/or mucosa and/or on a device intended to break the epithelial barrier.

Another object of the present invention relates to a method for prevention or prophylaxis of bacterial and/or fungal infections, in particular nosocomial infections, including a step of application of a composition according to the invention on the cutaneous surface and/or the mucous membrane whose epithelium is intended to be broken or injured, for example by a catheter, in particular a vascular or urinary catheter, or with a breach allowing the passage of bacteria and/or yeasts.

The composition according to the invention, and in particular a pharmaceutical composition, may be formulated in any manner appropriate to its final use.

It may be formulated in particular in a form making it suited for administration by local, oral (per os), rectal, pulmonary, intravenous, subcutaneous, cutaneous, intramuscular and/or intraperitoneal route. As such, it may include any suitable excipient.

The composition according to the invention may particularly be formulated in a form suitable for such administrations, and in particular for topical application or administration by injection.

The composition according to the invention may in particular be provided in the form of a liquid, an emulsion, a cream or a gel. In general, it is provided in any form allowing easy surface application, for example on the skin, on the mucosa or on a treated device.

Advantageously, and in particular for topical forms and/or forms for local use, for example cutaneous use, they may be provided in a form in which the composition does not run out too easily so as to remain on the substrate to which they are applied.

More particularly in the case of preventive use, the composition according to the invention, in particular a pharmaceutical composition, may be provided in a form allowing topical application, such as a cream, a pomade, a powder, a gel or an emulsion. Advantageously, the composition runs little or none at all, in particular at 37° C., in particular so that it remains in place at the desired location.

The composition according to the invention, in particular a pharmaceutical composition, may particularly be provided in hydrophobic form, i.e., free of water and/or of polar solvent.

The composition according to the invention, in particular when it is provided in gel form, may have a viscosity ranging from 500 cP to 2000 cP, in particular 750 cP to 1500 cP. Viscosity may be measured at 25° C. with a portable CPE-52 at 250 rpm.

The composition according to the invention, in particular a pharmaceutical composition, in particular in pomade, gel or cream form, may include polyethylene glycol, in particular macrogol 400, medium-chain triglycerides and/or soya oil, and in particular the composition includes only one of these compounds.

The composition according to the invention, in particular a pharmaceutical composition, may include a total proportion of these compounds ranging from 70% to 99%, in particular from 90% to 97% by weight in relation to the total weight of the composition.

Said composition may further include colloidal silica, in particular in a proportion ranging from 2% to 20% by weight, in particular from 3% to 10% by weight, or even roughly 5% by weight in relation to the total weight of the composition.

The composition according to the invention, in particular a pharmaceutical composition, may also be an emulsion, and in particular this emulsion includes a gelling agent.

The gelling agent may be a polymer, in particular polyvinyl pyrrolidone, in particular povidone, for example povidone K30®. The proportion of gelling agent may range from 40% to 60% by weight in relation to the total weight of the composition.

The emulsion may include a surfactant, for example such as polysorbate, polyglyceryl oleate or capric/caprylic acid glycerides. The proportion of surfactant may range from 1% to 5% by weight in relation to the total weight of the composition.

The emulsion may include water, in particular in a proportion ranging from 40% to 60% by weight in relation to the total weight of the composition.

The composition according to the invention may also be formulated with the aim of being able to be applied, in particular as a surface treatment, to invasive or noninvasive medical devices, implantable active medical devices such as prostheses or stents, and implantable devices. As such, it may include any suitable excipient.

According to a particular embodiment, the composition, in particular an antibacterial or pharmaceutical composition, also includes a broad-spectrum antiseptic, such as chlorhexidine or iodine, in particular povidone-iodine solution, for example Betadine®.

According to a particular embodiment, the invention has as an object a bandage or a patch including a composition according to the invention, in particular an antibacterial or pharmaceutical composition. Such a bandage or a patch is intended in particular to prevent nosocomial diseases, in particular in the case of catheter use.

In particular, said patch or bandage is packaged in a sterile manner.

According to another embodiment, in particular in the case of a preventive treatment or a surface treatment, the composition, in particular an antibacterial or pharmaceutical composition, is a cream, an emulsion, a pomade, a powder or a gel.

According to another embodiment, in particular in the case of a curative treatment, the composition, in particular an antibacterial or pharmaceutical composition, is formulated in such a way as to be able to be injected, in particular by intravenous, subcutaneous, transcutaneous, intramuscular and/or intraperitoneal route. The composition thus may be in the form of a hydrophobic or hydrophobic composition.

A hydrophilic composition may include a gelling agent, for example such as defined above, and/or a surfactant, in particular such as defined above.

A hydrophobic composition may include polyethylene glycol, in particular macrogol 400, medium-chain triglycerides and/or soya oil, optionally diluted in water.

According to another of its aspects, the invention has as an object the use of trans-cinnamaldehyde, in particular trans-cinnamaldehyde and at least one compound selected from trans-2-methoxycinnamaldehyde, cinnamyl acetate, coumarin, linalool, beta-caryophyllene, eugenol, cineole, benzyl benzoate and safrole, or at least one compound selected from trans-2-methoxycinnamaldehyde, cinnamyl acetate, coumarin, linalool and beta-caryophyllene, or a composition according to the invention, as an antibacterial active ingredient.

Said use may be in vivo or ex vivo.

According to another of its aspects, the invention also has as an object the use of trans-cinnamaldehyde, in particular trans-cinnamaldehyde and at least one compound selected from trans-2-methoxycinnamaldehyde, cinnamyl acetate, coumarin, linalool, beta-caryophyllene, eugenol, cineole, benzyl benzoate and safrole, or at least one compound selected from trans-2-methoxycinnamaldehyde, cinnamyl acetate, coumarin, linalool and beta-caryophyllene, or a composition according to the invention, for the preparation of an antibacterial active ingredient.

More particularly, the antibacterial active ingredient includes, or even consists of, at least two, in particular at least three, or even at least four, and even more particularly at least five of the compounds mentioned above.

According to a particular embodiment, the antibacterial active ingredient corresponds to the antibacterial composition, in particular to one or the other specific embodiment described above.

According to another of its aspects, the invention also has as an object the use of trans-cinnamaldehyde, in particular cinnamaldehyde and at least one compound selected from trans-2-methoxycinnamaldehyde, cinnamyl acetate, coumarin, linalool, beta-caryophyllene, eugenol, cineole, benzyl benzoate and safrole, or at least one compound selected from trans-2-methoxycinnamaldehyde, cinnamyl acetate, coumarin, linalool and beta-caryophyllene, or a composition according to the invention, for the preparation of a drug intended for the treatment or prevention of a nosocomial disease caused by an antibacterial-resistant bacterium in an animal, in particular in a mammal, and in particular in a human being.

According to another of its aspects, the invention has as an object a method for preparing a surface of the body, in particular skin or mucous membrane, or a surface of a device, for example an end of a catheter, including at least one step comprised of covering said surface with a composition according to the invention.

According to a particular embodiment, said method is not carried out on the body surface of an animal and in particular of a human being.

This method may make it possible to limit the risks of bacterial infections, and in particular of nosocomial infections.

In the case where a composition is applied to the skin, it may make it possible, if the cutaneous barrier is broken, to limit or even to prevent said bacteria, in particular a resistant bacteria, from infecting the body.

Of course, the various characteristics of the invention may be combined.

The examples which follow illustrate the invention and are not restrictive.

EXAMPLE 1

Agar Test Protocol

For bacteria to have good accessibility (aqueous phase multiplication only) to essential oils, it is essential to find a method of aqueous phase solubilization. This step is neglected in much work that directly uses the lipid phase, which is inaccessible to bacteria (oil-soaked disc placed on agar). Moreover, for the topical use of oils, this solubilization phase is also essential, and with the goal of practical application, surfactants and solubilization adjuvants are also selected for their satisfactory cutaneous tolerance.

Solubilization relies upon surfactants (Tween 20, Tween 80) and solubilization adjuvants (propylene glycol, glycerol, mannitol, ethanol, modified starch). However, the use of ethanol seems inappropriate (antibacterial, highly volatile). Preliminary tests with a mixture of Tween 80 and 20% propylene glycol yielded sufficient solubilization for most oils (10 g of essential oil, 29 g of Tween 80, 61 g of 20% molar propylene glycol). Before the first analyses, the surfactant and the solubilization adjuvant were tested in the proportions indicated to verify the absence of antibacterial activity. A strain of *E. coli* was inhibited by this mixture and thus the propylene glycol concentration was reduced to 10% molar: at this concentration no strain was inhibited.

The final preparation includes: 1.0 ml of essential oil, 3.4 ml of Tween 80 and 5.6 ml of 10% molar propylene glycol aqueous solution.

EXAMPLE 2

Bacterial Strains

The strains tested are isolated from various human samples (blood, urine, pulmonary aspiration, etc.). They were isolated from patients who were not infected upon entering the hospital and in whom an infection occurred after at least 48 hours of hospitalization.

The strains studied in the present example are as follows:
- *E. coli* ATCC 25922, for quality control (table 1),
- Strains of *Pseudomonas aeruginosa*: strains 8128, 8129, 8132, 8134 (table 2), and 9007 (presented in table 6),
- Strains of *E. coli*: strains 8154, 8155, 8156 and 8157 (table 3), and 9003 (table 6),
- Strains of golden staph (*S. aureus*): strains 8147, 8239 and 8240 (table 4),
- Strains of *Enterococcus*: 8152 and 8153 (table 5),
- Strain *Enterococcus faecium* (9001) (table 6),
- Strain *Enterobacter aerogenes* (9004) (table 6),
- Strain *Acinetobacter baumannii* (9010) (presented in table 6).

Three clinical categories were selected for interpretation of the in vitro sensitivity tests: sensitive (S), resistant (R) and intermediate (I).

The strains categorized S are those for which the probability of therapeutic success is high in the case of treatment by systemic route with the dosing schedule recommended in the summary of product characteristics (SPC) prepared by the French Health Products Safety Agency (AFSSAPS).

The strains categorized R are those for which there is a high probability of therapeutic failure regardless of treatment type and antibiotic dose.

The strains categorized I are those for which therapeutic success cannot be predicted. These strains form a heterogeneous group for which the results obtained in vitro are not predictive of therapeutic success. Indeed, these strains:
- may exhibit a resistance mechanism whose expression in vitro is low, with the consequence that they are categorized in category S. However, in vivo, some of these strains appear resistant to the treatment;
- may exhibit a resistance mechanism whose expression is insufficient to justify categorization in category R, but is sufficiently low to offer the hope of a therapeutic effect under certain conditions (high local concentrations or higher doses).

The intermediate category is also a buffer zone which takes into account technical and biological uncertainties.

Methodology

The sensitivity of strains to antibiotics was determined by a diffusion technique according to the 2008 recommendations by the Antibiogram Committee of the French Microbiology Society (CA-SFM).

Establishment of Critical Values Delimiting the Clinical Categories

The critical values for concentrations and diameters defined for each antibiotic are established by taking into account several parameters:
- distribution of minimum inhibitory concentrations (MIC) for defined populations of strains belonging to each bacterial species involved in human pathology;
- humoral and tissue concentrations obtained with the dosing schedules recommended in the summary of product characteristics (SPC);
- comparison of the results obtained in vitro and the results obtained in vivo (clinical trials);
- statistical variability of the methods used to measure MIC and inhibition zone diameters.

Two critical concentrations are thus defined: the lower critical concentration c and the upper critical concentration C, which correspond to the critical diameters D and d, respectively.

Strain Categorization Procedure and Criteria

In terms of critical concentrations and diameters, strains are categorized as follows:
- sensitive (S): strains for which the MIC of the antibiotic tested is less than or equal to the lower critical concentration c, which is equivalent to a diameter greater than or equal to the critical diameter D;
- resistant (R): strains for which the MIC of the antibiotic tested are greater than the upper critical concentration C, corresponding to a diameter less than the critical diameter d;
- intermediate sensitivity (I): strains for which the MIC of the antibiotic tested and the corresponding diameter are between the two critical concentrations and the two critical diameters.

The tests were carried out on Mueller-Hinton agar. An inoculum adjusted to 0.5 on the McFarland scale is then diluted to 1/100. Petri dishes are inoculated by swabbing. The dishes are read after 24 hours of incubation at 37° C.

The raw results are then interpreted according to the interpretative reading rules of the CA-SFM. Two examples: all strains of methicillin-resistant *Staphylococcus* are resistant to all beta-lactams, and the same is true for gentamicin-resistant strains; golden staph is necessarily resistant to kanamycin (and amikacin) and tobramycin.

The quality of the diffusion method is controlled using *E. coli* strain ATCC 25922.

Results of the Antibiogram:
Quality control (table 1)

TABLE 1

| Quality control *E. coli* ATCC 25922 | | |
|---|---|---|
| Antibiotics | Diameter (D) | Category (Cat.) |
| PENICILLINS | | |
| Amoxicillin | 23 | S |
| Amoxicillin + clavulanic acid | 22 | S |
| Ticarcillin | 25 | S |
| CEPHALOSPORINS | | |
| Cefalotin | 20 | S |
| Ceftazidime | 25 | S |
| Cefepime | 25 | S |
| Cefoxitin | 24 | S |
| AMINOGLYCOSIDES | | |
| Kanamycin | 22 | S |
| Gentamicin | 25 | S |
| Tobramycin | 24 | S |
| CARBAPENEMS | | |
| Imipenem | 34 | S |
| QUINOLONES | | |
| Nalidixic acid | 28 | S |
| FLUOROQUINOLONES | | |
| Levofloxacin | 31 | S |

For the quality control strain, the diameters are in conformity.

Strains of *Pseudomonas aeruginosa* (table 2)

TABLE 2

| Strains 8128, 8129, 8132 and 8134 | | | | | | | | |
|---|---|---|---|---|---|---|---|---|
| | 8128 | | 8129 | | 8132 | | 8134 | |
| Antibiotics | D | Cat. | D | Cat. | D | Cat. | D | Cat. |
| PENICILLINS | | | | | | | | |
| Amoxicillin | 0 | R | 0 | R | 0 | R | 0 | R |
| Amoxicillin + clavulanic acid | 0 | R | 0 | R | 0 | R | 0 | R |
| Ticarcillin | 21 | I | 13 | R | 12 | R | 23 | S |
| CEPHALOSPORINS | | | | | | | | |
| Cefalotin | 0 | R | 0 | R | 0 | R | 0 | R |
| Ceftazidime | 25 | S | 0 | R | 26 | S | 25 | S |
| Cefepime | 30 | S | 27 | S | 25 | S | 29 | S |
| Cefoxitin | 0 | R | 0 | R | 0 | R | 0 | R |
| AMINOGLYCOSIDES | | | | | | | | |
| Kanamycin | 9 | R | 10 | R | 0 | R | 14 | R |
| Gentamicin | 27 | S | 21 | R | 16 | R | 0 | R |
| Tobramycin | 30 | S | 27 | S | 0 | R | 11 | R |
| CARBAPENEMS | | | | | | | | |
| Imipenem | 18 | I | 36 | S | 13 | R | 26 | S |
| QUINOLONES | | | | | | | | |
| Nalidixic acid | 0 | R | 0 | R | 0 | R | 0 | R |
| FLUOROQUINOLONES | | | | | | | | |
| Levofloxacin | 23 | S | 26 | S | 0 | R | 0 | R |

It is noted that:
Strain 8128 is multiresistant. It is also resistant to penicillins and quinolones.
Strain 8129 hyperproduces chromosomal cephalosporinase. It is also resistant to penicillins and quinolones.
Strain 8132 is multiresistant (D2 porin defect).
Strain 8134 is resistant to quinolones, fluoroquinolones and aminoglycosides.

Strains of *E. coli* (table 3)

TABLE 3

| Strains 8154, 8155, 8156 and 8157 | | | | | | | | |
|---|---|---|---|---|---|---|---|---|
| | 8154 | | 8155 | | 8156 | | 8157 | |
| Antibiotics | D | Cat. | D | Cat. | D | Cat. | D | Cat. |
| PENICILLINS | | | | | | | | |
| Amoxicillin | 0 | R | 24 | S | 25 | S | 0 | R |
| Amoxicillin + clavulanic acid | 14 | S | 24 | S | 22 | S | 30 | S |
| Ticarcillin | 0 | R | 31 | S | 28 | S | 0 | R |
| CEPHALOSPORINS | | | | | | | | |
| Cefalotin | 21 | S | 21 | S | 20 | S | 19 | S |
| Ceftazidime | 30 | S | 30 | S | 33 | S | 30 | S |
| Cefepime | 32 | S | 35 | S | 32 | S | 32 | S |
| Cefoxitin | 26 | S | 25 | S | 26 | S | 30 | S |
| AMINOGLYCOSIDES | | | | | | | | |
| Kanamycin | 24 | S | 23 | S | 27 | S | 24 | S |
| Gentamicin | 21 | S | 21 | S | 25 | S | 25 | S |
| Tobramycin | 24 | S | 24 | S | 22 | S | 24 | S |
| CARBAPENEMS | | | | | | | | |
| Imipenem | 33 | S | 34 | S | 34 | S | 20 | I |
| QUINOLONES | | | | | | | | |
| Nalidixic acid | 24 | S | 28 | S | 27 | S | 0 | R |
| FLUOROQUINOLONES | | | | | | | | |
| Levofloxacin | 36 | S | 31 | S | 31 | S | 11 | R |

It is noted that:
Strain 8154 produces penicillinase.
Strain 8155 is nonresistant.
Strain 8156 is nonresistant.
Strain 8157 produces penicillinase and is fluoroquinolone resistant.

Strains of golden staph (*S. aureus*) (table 4)

TABLE 4

| Strains 8147, 8239 and 8240 | | | | | | |
|---|---|---|---|---|---|---|
| | 8147 | | 8239 | | 8240 | |
| Antibiotics | D | Cat. | D | Cat. | D | Cat. |
| PENICILLINS | | | | | | |
| Amoxicillin | 26 | R | 12 | R | 17 | R |
| Amoxicillin + clavulanic acid | 25 | R | 27 | R | 25 | R |
| CEPHALOSPORINS | | | | | | |
| Cefalotin | 17 | R | 17 | R | 17 | R |
| AMINOGLYCOSIDES | | | | | | |
| Kanamycin | 22 | S | 26 | S | 12 | R |
| Gentamicin | 26 | S | 28 | S | 27 | S |
| Tobramycin | 30 | S | 31 | S | 0 | R |
| FLUOROQUINOLONES | | | | | | |
| Levofloxacin | 10 | R | 10 | R | 0 | R |
| LINCOSAMIDES | | | | | | |
| Clindamycin | 29 | S | 31 | S | 30 | S |
| STREPTOGRAMINS | | | | | | |
| Pristinamycin | 29 | S | 32 | S | 27 | S |

It is noted that:
Strain 8147 is methicillin sensitive.
Strain 8239 is methicillin resistant.
Strain 8240 is methicillin resistant and fluoroquinolone resistant.

Strains of *Enterococcus* (table 5)

TABLE 5

Strains 8152 and 8153

| | 8152 | | 8153 | |
|---|---|---|---|---|
| Antibiotics | Diameter | Category | Diameter | Category |
| PENICILLINS | | | | |
| Amoxicillin | 32 | S | 33 | S |
| Amoxicillin + clavulanic acid | 30 | S | 32 | S |
| CEPHALOSPORINS | | | | |
| Cefoxitin | 0 | R | 25 | S |
| AMINOGLYCOSIDES | | | | |
| Kanamycin | 10 | R | 14 | R |
| Gentamicin | 15 | R | 14 | R |
| Tobramycin | 11 | R | 14 | R |
| FLUOROQUINOLONES | | | | |
| Levofloxacin | 29 | S | 26 | S |
| LINCOSAMIDES | | | | |
| Clindamycin | 0 | R | 0 | R |
| STREPTOGRAMINS | | | | |
| Pristinamycin | 23 | S | 22 | S |

The two strains have natural resistance and aminoglycoside resistance (low level). Moreover, they are MLSB-resistant (resistant to erythromycin and clindamycin and sensitive to pristinamycin).

Strains selected for their multiresistance (table 6)

TABLE 6

Strains 9001, 9003 and 9004

| 9001 *Enterobacter faecium* | | 9003 *E. Coli* | | 9004 *Enterobacter aerogenes* | |
|---|---|---|---|---|---|
| Pen G | nl | Amox | R | Amox | R |
| Ampi | R | Augmentin | S | Augmentin | R |
| Kana HC | R | Ticar | R | Ticar | R |
| Genta HC | S | Claventin | R | Claventin | R |
| Strepto HC | R | Pipera-tazo | S | Pipera-tazo | S |
| Tetra | S | Cefalotin | R | Cefalotin | R |
| Erythro | R | Cefotaxime | R | Cefotaxime | R |
| Clinda 2 | R | Cefepime | R | Cefepime | R |
| Dalf-quinu | I | Ceftazidime | R | Ceftazidime | R |
| Linezolid | S | Imipenem | S | Imipenem | S |
| Levoflo | R | Eratpenem | S | Eratpenem | S |
| Moxiflo | R | Gentamicin | S | Gentamicin | S |
| Trim + Sulf | R | Tobramycin | S | Tobramycin | R |
| Teico | S | Amikacin | S | Amikacin | I |
| Vanco | R | Colimycin | S | Colimycin | S |
| Furans | S | Bactrim | S | Bactrim | R |
| Chloram | S | Noroxin | R | Noroxin | R |
| | | Ciprofloxacin | R | Ciprofloxacin | R |

Two genetically defined strains were also tested:

strain 9007, *Pseudomonas aeruginosa*, with VIM-2 carbapenemase, table 7, and strain 9010, *Acinetobacter baumannii*, with VEB-1 ESBL, table 7.

TABLE 7

Strains 9007 and 9010

| | 9007 *Pseudomonas aeruginosa* | 9010 *Acinetobacter* |
|---|---|---|
| AMOXICILLIN | R | R |
| AMOXICILLIN-clavu | R | R |
| CEFALOTIN | R | R |
| TICARCILLIN | R | R |
| CEFTAZIDIME | S | R |
| CEFEPIME | S | R |
| CEFOXITIN | R | R |
| KANAMYCIN | R | R |
| GENTAMICIN | S | R |
| TOBRAMYCIN | S | R |
| IMIPENEM | R | S |
| NALIDIXIC ACID | R | R |
| LEVOFLOXACIN | S | R |

EXAMPLE 3

Trans-Cinnamaldehyde

Materials:
Bacterial strains (those described in example 2)
Brain-heart (BH) broth
Mueller-Hinton agar (MHA, in inclined test tubes or in test tubes containing 18 ml and 19 ml)
Ringer's solution containing cysteine (RC)
Falcon test tubes for dilutions
Sterile test tubes
Trans-cinnamaldehyde Protocol:
The day before the test, inoculate the strains in BH medium and on tilted MHA. Prepare test tubes containing 19 ml and 18 ml of MHA. Prepare test tubes containing 5 ml of 10% molar propylene glycol for the various dilutions.

On the day of the test, solubilize the trans-cinnamaldehyde as follows:
1 ml of trans-cinnamaldehyde
3.4 ml of Tween 80
5.6 ml of 10% molar propylene glycol.

Prepare the mixture of Tween 80 and 10% molar propylene glycol in advance. Place 9 ml of this mixture in Falcon test tubes and add 1 ml of oil.

When the trans-cinnamaldehyde is solubilized, prepare successive 1/2 dilutions in 10% molar propylene glycol.

Add 1 ml of suitable dilutions in the test tubes containing 19 ml of medium, homogenize well and pour into Petri dishes. For the first dilution (10% volume of trans-cinnamaldehyde), prepare a test tube of 18 ml of MHA and 2 ml of 10% volume trans-cinnamaldehyde to increase the highest concentration to be tested (1% volume).

Preparation of the Inoculum:
Add 10 ml of RC to the inclined agar that contains the strain and then take up 1 drop of this suspension and distribute it in a test tube containing 10 ml of RC: a $10^6$ CFU/ml suspension is obtained. Place 1 ml of this suspension in the Steers cup (the 33 strains are inoculated on the same dish). Inoculate each dish and incubate for 24 hours at 37° C.

Control dishes (MHA alone) are also prepared to verify that all strains are growing and that there is no problem of contamination.

Results:
The results obtained with the various strains are presented in table 8 below:

TABLE 8

Antibacterial activity of trans-cinnamaldehyde

| Ref. | Name | 1 | 0.5 | 0.25 | 0.125 | 0.06 | 0.03 | 0.015 | 0.0075 | 0.0038 |
|---|---|---|---|---|---|---|---|---|---|---|
| ATCC 25922 | E. coli | − | − | − | − | − | − | − | + | + |
| 8128 | Pseudomonas | − | − | − | − | − | + | + | + | + |
| 8129 | Pseudomonas | − | − | − | − | − | + | + | + | + |
| 8132 | Pseudomonas | − | − | − | − | + | + | + | + | + |
| 8134 | Pseudomonas | − | − | − | − | − | − | − | + | + |
| 8154 | E. coli | − | − | − | − | − | − | + | + | + |
| 8155 | E. coli | − | − | − | − | − | − | + | + | + |
| 8156 | E. coli | − | − | − | − | − | − | + | + | + |
| 8157 | E. coli | − | − | − | − | − | − | + | + | + |
| 8147 | Staphylococcus | − | − | − | − | − | − | + | + | + |
| 8239 | Staphylococcus | − | − | − | − | − | − | + | + | + |
| 8240 | Staphylococcus | − | − | − | − | − | − | + | + | + |
| 8152 | Enterococcus | − | − | − | − | − | − | + | + | + |
| 8153 | Enterococcus | − | − | − | − | − | − | + | + | + |
| 9001 | Enterococcus | − | − | − | − | − | − | + | + | + |
| 9003 | E. coli | − | − | − | − | − | + | + | + | + |
| 9004 | Enterobacter | − | − | − | − | − | + | + | + | + |
| 9007 | P. aeruginosa | − | − | − | − | − | + | + | + | + |
| 9010 | A. baumannii | − | − | − | − | − | − | − | + | + |

It is noted that trans-cinnamaldehyde exhibits antibacterial activity on both Gram-positive bacteria and Gram-negative bacteria. This effect is also observed on resistant strains. Moreover, this effect is observed at low volume concentrations.

Uncertainty is ± one dilution.

EXAMPLE 4

Essential Oil of Chinese Cinnamon

Example 3 is repeated but trans-cinnamaldehyde is replaced by a natural essential oil of Chinese cinnamon.
Results:
The results obtained with the various strains are presented in table 9 below:

TABLE 9

Antibacterial activity of essential oil of Chinese cinnamon

| Reference | Name | 1 | 0.5 | 0.25 | 0.125 | 0.06 | 0.03 |
|---|---|---|---|---|---|---|---|
| ATCC 25922 | E. coli | − | − | − | − | − | − |
| 8128 | Pseudomonas | − | − | − | − | + | + |
| 8129 | Pseudomonas | − | − | − | − | + | + |
| 8132 | Pseudomonas | − | − | − | + | + | + |
| 8134 | Pseudomonas | − | − | − | − | + | + |
| 8154 | E. coli | − | − | − | − | − | + |
| 8155 | E. coli | − | − | − | − | − | + |
| 8156 | E. coli | − | − | − | − | − | + |
| 8157 | E. coli | − | − | − | − | − | + |
| 8147 | Staphylococcus | − | − | − | − | − | + |
| 8239 | Staphylococcus | − | − | − | − | − | + |
| 8240 | Staphylococcus | − | − | − | − | − | + |
| 8152 | Enterococcus | − | − | − | − | − | + |
| 8153 | Enterococcus | − | − | − | − | − | + |
| 9001 | Enterococcus | − | − | − | − | − | − |
| 9003 | E. coli | − | − | − | − | − | − |
| 9004 | Enterobacter | − | − | − | − | − | + |
| 9007 | P. aeruginosa | − | − | − | − | + | + |
| 9010 | A. baumannii | − | − | − | − | − | − |

It is noted that essential oil of Chinese cinnamon exhibits antibacterial activity on both Gram-positive bacteria and Gram-negative bacteria. This effect is also observed on resistant strains. Moreover, this effect is observed at low volume concentrations.

Uncertainty is ± one dilution.

EXAMPLE 5

Essential Oil of Cinnamon Bark

Example 3 is repeated but trans-cinnamaldehyde is replaced by a natural essential oil of cinnamon bark.
Results:
The results obtained with the various strains are presented in table 9 below:

TABLE 10

Antibacterial activity of essential oil of cinnamon bark

| Ref. | Name | 1 | 0.5 | 0.25 | 0.125 | 0.06 | 0.03 | 0.015 | 0.0075 | 0.0038 |
|---|---|---|---|---|---|---|---|---|---|---|
| ATCC 25922 | E. coli | − | − | − | − | − | + | + | + | + |
| 8128 | Pseudomonas | − | − | − | − | + | + | + | + | + |
| 8129 | Pseudomonas | − | − | − | − | + | + | + | + | + |
| 8132 | Pseudomonas | − | − | − | + | + | + | + | + | + |
| 8134 | Pseudomonas | − | − | − | − | + | + | + | + | + |
| 8154 | E. coli | − | − | − | − | − | + | + | + | + |
| 8155 | E. coli | − | − | − | − | − | + | + | + | + |

TABLE 10-continued

Antibacterial activity of essential oil of cinnamon bark

| Ref. | Name | 1 | 0.5 | 0.25 | 0.125 | 0.06 | 0.03 | 0.015 | 0.0075 | 0.0038 |
|---|---|---|---|---|---|---|---|---|---|---|
| 8156 | E. coli | − | − | − | − | − | + | + | + | + |
| 8157 | E. coli | − | − | − | − | − | + | + | + | + |
| 8147 | Staphylococcus | − | − | − | − | − | + | + | + | + |
| 8239 | Staphylococcus | − | − | − | − | − | + | + | + | + |
| 8240 | Staphylococcus | − | − | − | − | − | + | + | + | + |
| 8152 | Enterococcus | − | − | − | − | − | + | + | + | + |
| 8153 | Enterococcus | − | − | − | − | − | + | + | + | + |
| 9001 | Enterococcus | − | − | − | − | − | + | + | + | + |
| 9003 | E. coli | − | − | − | − | − | + | + | + | + |
| 9004 | Enterobacter | − | − | − | − | + | + | + | + | + |
| 9007 | P. aeruginosa | − | − | − | − | + | + | + | + | + |
| 9010 | A. baumannii | − | − | − | − | − | + | + | + | + |

It is noted that essential oil of cinnamon bark exhibits antibacterial activity on both Gram-positive bacteria and Gram-negative bacteria. This effect is also observed on resistant strains. Moreover, this effect is observed at low volume concentrations.

Uncertainty is ± one dilution.

EXAMPLE 6

Combinations of Essential Oil of Chinese Cinnamon and Essential Oil of Cinnamon Bark Example 3 is repeated but trans-cinnamaldehyde is replaced by a 1:1 (volume), 1:2 (volume) or 2:1 (volume) mixture of natural essential oil of Chinese cinnamon and natural essential oil of cinnamon bark.

In the 1:1 mixture the two oils are present in a proportion of 1% each and in the 2:1 mixture the first oil is present in a proportion of 1.3% and the second in a proportion of 0.7%. These percentages are % in volume in relation to the total volume.

Results:

The results obtained with the various strains are presented in tables 11 to 13 below:

TABLE 11

Antibacterial activity of the combination of essential oil of cinnamon bark and essential oil of Chinese cinnamon (1:1)

| Ref. | Name | 1 | 0.5 | 0.25 | 0.125 | 0.06 | 0.03 | 0.015 | 0.0075 | 0.0038 |
|---|---|---|---|---|---|---|---|---|---|---|
| ATCC 25922 | E. coli | − | − | − | − | − | − | − | + | + |
| 8128 | Pseudomonas | − | − | − | − | − | − | + | + | + |
| 8129 | Pseudomonas | − | − | − | − | − | − | + | + | + |
| 8132 | Pseudomonas | − | − | − | − | − | + | + | + | + |
| 8134 | Pseudomonas | − | − | − | − | − | − | + | + | + |
| 8154 | E. coli | − | − | − | − | − | − | − | + | + |
| 8155 | E. coli | − | − | − | − | − | − | − | + | + |
| 8156 | E. coli | − | − | − | − | − | − | − | + | + |
| 8157 | E. coli | − | − | − | − | − | − | − | + | + |
| 8147 | Staphylococcus | − | − | − | − | − | − | − | + | + |
| 8239 | Staphylococcus | − | − | − | − | − | − | − | + | + |
| 8240 | Staphylococcus | − | − | − | − | − | − | − | + | + |
| 8152 | Enterococcus | − | − | − | − | − | − | − | + | + |
| 8153 | Enterococcus | − | − | − | − | − | − | − | − | + |
| 9001 | Enterococcus | − | − | − | − | − | − | − | − | + |
| 9003 | E. coli | − | − | − | − | − | − | − | − | + |
| 9004 | Enterobacter | − | − | − | − | − | − | − | + | + |
| 9007 | P. aeruginosa | − | − | − | − | − | − | − | − | + |
| 9010 | A. baumannii | − | − | − | − | − | − | − | − | − |

TABLE 12

Antibacterial activity of the combination of essential oil of cinnamon bark and essential oil of Chinese cinnamon (2:1)

| Ref. | Name | 1 | 0.5 | 0.25 | 0.125 | 0.06 | 0.03 | 0.015 | 0.0075 | 0.0038 |
|---|---|---|---|---|---|---|---|---|---|---|
| ATCC 25922 | E. coli | − | − | − | − | − | − | − | + | + |
| 8128 | Pseudomonas | − | − | − | − | − | + | + | + | + |
| 8129 | Pseudomonas | − | − | − | − | − | + | + | + | + |

TABLE 12-continued

Antibacterial activity of the combination of essential oil of cinnamon bark and essential oil of Chinese cinnamon (2:1)

| Ref. | Name | 1 | 0.5 | 0.25 | 0.125 | 0.06 | 0.03 | 0.015 | 0.0075 | 0.0038 |
|---|---|---|---|---|---|---|---|---|---|---|
| 8132 | Pseudomonas | − | − | − | − | + | + | + | + | + |
| 8134 | Pseudomonas | − | − | − | − | − | + | + | + | + |
| 8154 | E. coli | − | − | − | − | − | − | + | + | + |
| 8155 | E. coli | − | − | − | − | − | − | + | + | + |
| 8156 | E. coli | − | − | − | − | − | − | − | + | + |
| 8157 | E. coli | − | − | − | − | − | − | − | + | + |
| 8147 | Staphylococcus | − | − | − | − | − | − | + | + | + |
| 8239 | Staphylococcus | − | − | − | − | − | − | + | + | + |
| 8240 | Staphylococcus | − | − | − | − | − | − | + | + | + |
| 8152 | Enterococcus | − | − | − | − | − | + | + | + | + |
| 8153 | Enterococcus | − | − | − | − | − | + | + | + | + |

TABLE 13

Antibacterial activity of the combination of essential oil of cinnamon bark and essential oil of Chinese cinnamon (1:2)

| Ref. | Name | 1 | 0.5 | 0.25 | 0.125 | 0.06 | 0.03 | 0.015 | 0.0075 | 0.0038 |
|---|---|---|---|---|---|---|---|---|---|---|
| ATCC 25922 | E. coli | − | − | − | − | − | + | + | + | + |
| 8128 | Pseudomonas | − | − | − | − | + | + | + | + | + |
| 8129 | Pseudomonas | − | − | − | − | + | + | + | + | + |
| 8132 | Pseudomonas | − | − | − | + | + | + | + | + | + |
| 8134 | Pseudomonas | − | − | − | − | + | + | + | + | + |
| 8154 | E. coli | − | − | − | − | − | + | + | + | + |
| 8155 | E. coli | − | − | − | − | − | + | + | + | + |
| 8156 | E. coli | − | − | − | − | − | + | + | + | + |
| 8157 | E. coli | − | − | − | − | − | + | + | + | + |
| 8147 | Staphylococcus | − | − | − | − | − | + | + | + | + |
| 8239 | Staphylococcus | − | − | − | − | − | + | + | + | + |
| 8240 | Staphylococcus | − | − | − | − | − | + | + | + | + |
| 8152 | Enterococcus | − | − | − | − | − | + | + | + | + |
| 8153 | Enterococcus | − | − | − | − | − | + | + | + | + |

It is noted that the combination of essential oil of cinnamon bark and essential oil of Chinese cinnamon exhibits antibacterial activity on both Gram-positive bacteria and Gram-negative bacteria. This effect is also observed on resistant strains. Moreover, this effect is observed at low volume concentrations, even lower than those observed for each essential oil alone. The best results are obtained with a 1:1 volume ratio.

Uncertainty is ± one dilution.

EXAMPLE 7

Bactericidal Effect

Preparation of the Essential Oil Suspension

A mixture containing 3.4 ml of Tween 80 and 5.6 ml of propylene glycol is prepared and 1 ml of oil (10% final concentration) is added to this mixture.

Preparation of the Inoculum and the Oil/Bacteria Mixture

After culturing for 24 hours in Mueller-Hinton broth, the inoculum is adjusted to approximately $10^8$ CFU/ml, which corresponds to turbidity comparable to a 0.5 McFarland standard. By dilution to 1/10, a test tube containing 9 ml of a $10^7$ CFU/ml bacterial suspension in Ringer's solution containing cysteine is then prepared to which is added either 1 ml of distilled water (control) or 1 ml of the 10% oil suspension (1% final concentration of oil).

Enumeration of Bacteria

The bacteria are enumerated by successive 1/10 dilutions of the samples. 100 µl of each dilution is spread over Mueller-Hinton agar. Enumeration is carried out on the Petri dish that contains between 15 and 150 colonies. The enumeration threshold is thus 150 CFU/ml.

Neutralizing Capacity of Dey-Engley Broth

To stop the activity of the oil after a defined period of contact, 100 µl of the oil/bacteria mixture is withdrawn and then diluted in 900 µl of neutralizing broth in order to block the antibacterial action of the oil.

The neutralizing broth used is the "Neutralizing broth for neutralizing and testing disinfectants and antiseptics" of Dey and Engley, sold by Criterion, of the following formula:
   glucose (10 g)
   lecithin (7 g)
   casein peptone (5 g)
   Tween 80 (5 g)
   sodium thiosulfate (6 g)
   dipotassium phosphate (3.3 g)
   sodium bisulfite (2.5 g)
   yeast extract (2.5 g)
   sodium thioglycollate (1 g)
   monopotassium phosphate (0.1 g)
   bromocresol purple (20 mg).

The powder obtained is dissolved in one liter of deionized water, and then after heating and dissolution the medium is sterilized by autoclaving at 121° C. for 15 minutes. The final pH is 7.6±0.2.

A neutralizing control is prepared as follows:

A mixture of equal parts oil and neutralizing broth is brought together with the bacterial inoculum. After incubation for 48 hours at 37° C., the bacterial enumeration must not be less than 50% of the control enumeration. This makes it possible to demonstrate the absence of antibacterial activity by the neutralizing broth and especially the fact that the neutralizing broth completely blocks the antibacterial action of the oil, thus avoiding the phenomenon of carry-over.

Determination of the Starting Inoculum

Enumeration is carried out at $T_0$. 100 µl of the starting inoculum is withdrawn and then placed in 900 µl of diluent. Next, 100 µl of each of six subsequent 1/10 dilutions is deposited on Mueller-Hinton agar. After incubation of the Petri dishes for 48 hours at 37° C., the colonies on the agar are counted as indicated above.

Measurement of the Bactericidal Activity of the Essential Oils

After the oil/bacteria mixture is in contact for 15, 30, 45 and 60 minutes, 100 µl of the oil/bacteria mixture is withdrawn, placed in 900 µl of neutralizing broth and then diluted to 1/10 and 1/100 in Ringer's solution containing cysteine. Next, 100 µl of each dilution is spread over Mueller-Hinton agar. The dishes are then incubated for 48 hours and the surviving colonies counted.

Expression of Results

By definition, a bactericidal effect is obtained if a drop of at least 3 logarithms from the starting inoculum is observed. A curve of bactericidal effect relating number of bacteria to contact time with oil may be plotted. Such a curve makes it possible to see whether the kinetics of the bactericidal effect is intense and rapid or not.

Results:

The composition including a 1:1 ratio of essential oil of Chinese cinnamon and essential oil of cinnamon bark (as described in example 6) exhibits a bactericidal effect with respect to strains 8132, 8154, 8152, 8155, ATCC 25922 (control), 9004 and 9001, identified more precisely in the examples above.

This composition also exhibits bactericidal activity on the following strains, characterized by the method described above:

*Staphylococcus aureus* 8148: strain resistant to methicillin and to fluoroquinolones,

*Staphylococcus aureus* 8237: wild strain.

EXAMPLE 8

Antibacterial Gel 1 ml of a 1:1 mixture of essential oil of Chinese cinnamon and essential oil of Ceylon cinnamon is solubilized in 93 ml of macrogol 400 (Lutrol® E 400). Next, 6 g of colloidal silica is added.

The totality is homogenized in order to obtain a non-running gel with a viscosity (T48) of 798 cP at 25° C., portable CPE-52, at 250 rpm.

This gel may in particular be used to prevent bacterial and/or fungal infections, for example in the case of catheter use.

Said catheter may be covered by said gel, or a surface with a cutaneous breach or a mucous membrane likely to be injured may be covered with said gel.

Such a gel makes it possible in particular to reduce the bacterial content of a topical form.

EXAMPLE 9

Treatment of Infected Mice

The test is carried out on 10- to 12-week-old BALB/c mice.

Eight mice are infected by intraperitoneal injection of $4·10^7$ methicillin-resistant *Staphylococcus aureus* in growth phase.

The following day, a daily treatment of 100 mg/kg/d (in one administration) is begun with the following conditions:

Absence of treatment

Essential oil of Ceylon cinnamon

Essential oil of Ceylon cinnamon+essential oil of Chinese cinnamon (1:1)

TABLE 15

| Survival of mice after inoculation with MRSA | | | | |
|---|---|---|---|---|
| Surviving mice | Day 1 | Day 2 | Day 3 | Day 4 |
| Absence of treatment | 8/8 | 7/8 | 7/8 | 4/8 |
| Ceylon cinnamon/Chinese cinnamon mixture | 8/8 | 8/8 | 8/8 | 8/8 |
| Ceylon cinnamon | 8/8 | 8/8 | 8/8 | 8/8 |

It is further observed that the mice have a higher average weight in the Ceylon cinnamon/Chinese cinnamon mixture group, which tends to show that the mice treated with the mixture of essential oils respond better than those treated with Ceylon cinnamon alone.

This example demonstrates that effectiveness in vivo corresponds to effectiveness in vitro.

The invention claimed is:

1. Antibacterial composition comprising a synergistic combination of essential oil of Chinese cinnamon and essential oil of cinnamon bark, wherein the proportion of essential oil of Chinese cinnamon and essential oil of cinnamon bark ranges from 9:1 to 1:9 in volume V:V.

2. Pharmaceutical composition or drug comprising a composition such as defined according to claim 1.

3. Method for treating a disease comprising the administration to a patient in need thereof of an effective amount of pharmaceutical composition or drug according to claim 2.

4. Method according to claim 3, wherein the disease is a bacterial infection caused by anaerobic bacteria.

5. Method according to claim 3, wherein the disease is a nosocomial disease.

6. Method according to claim 3, wherein said bacterium is a resistant Gram-negative bacterium selected from the group consisting of the genus *Pseudomonas, Acinetobacter, Escherichia,* and *Enterobacter.*

7. Method according to claim 3, wherein said bacterium is a resistant Gram-positive bacterium of the genus *Staphylococcus* or of the genus *Enterococcus.*

8. Method according to claim 5, wherein said nosocomial disease is selected from the group consisting of urinary tract infections, respiratory system infections, digestive system infections, central nervous system infections, skin and soft tissue infections, bone, joint and muscle infections, vascular system infections, septic shock, diabetic foot and eschars.

9. Method according to claim 3, wherein said patients are immunosuppressed or immunodeficient individuals.

10. Method for disinfecting a surface, comprising at least one step consisting of covering said surface with a composition such as defined according to claim 1.

11. Composition according to claim 1, wherein the proportion of essential oil of Chinese cinnamon and essential oil of cinnamon bark ranges from 2:1 to 1:2 in volume V:V.

12. Composition according to claim 11, wherein the proportion of essential oil of Chinese cinnamon and essential oil of cinnamon bark is 1:1 in volume V:V.

13. Method according to claim 3, wherein said pharmaceutical composition or drug is intended for the treatment of bacterial infections.

14. Method according to claim 13, wherein the treatment of bacterial infection is broad spectrum.

15. Method according to claim 13, wherein the bacterial infection is caused by an antibacterial-resistant bacterium.

16. Method according to claim 3, wherein the patient is an animal.

17. Method according to claim 16, wherein the animal is a mammal.

18. Method according to claim 17, wherein the mammal is a human being.

19. Method according to claim 9, wherein the immunodeficient individuals are selected from the group consisting of the elderly, infants, young children, patients undergoing corticosteroid therapy, transplant patients and AIDS patients.

20. Method according to claim 10, wherein the surface is skin, mucous membrane or the surface of a device.

21. Method according to claim 20, wherein the surface of the device is the end of a catheter.

22. Method of preserving a food stuff comprising adding the composition according to claim 1 to the food stuff thereby preserving the food stuff from the bacteria.

23. Method of disinfecting a surface from bacteria treating said surface with a composition according to claim 1 thereby disinfecting the surface.

24. Composition according to claim 1, wherein the proportion of essential oil of Chinese cinnamon and essential oil of cinnamon bark is 4:1 to 1:4 in volume V:V.

25. Composition according to claim 1, wherein the proportion of essential oil of Chinese cinnamon and essential oil of cinnamon bark is 9:1 to 1:1 in volume V:V.

26. Composition according to claim 25, wherein the proportion of essential oil of Chinese cinnamon and essential oil of cinnamon bark is 4:1 to 1:1 in volume V:V.

27. Composition according to claim 26, wherein the proportion of essential oil of Chinese cinnamon and essential oil of cinnamon bark is 2:1 to 1:1 in volume V:V.

28. Composition according to claim 1, comprising:
trans-cinnamaldehyde, in a proportion ranging from 40% to 90% by weight in relation to the total weight of the composition,
cinnamyl acetate in a proportion ranging from 0.1% to 8% by weight in relation to the total weight of the composition,
trans-2-methoxycinnamaldehyde in a proportion ranging from 1% to 10% by weight in relation to the total weight of the composition,
linalool in a proportion ranging from 0.1% to 8% by weight in relation to the total weight of the composition,
beta-caryophyllene in a proportion ranging from 0.1% to 5% by weight in relation to the total weight of the composition,
benzyl benzoate in a proportion ranging from 0.01% to 3% by weight in relation to the total weight of the composition,
cineole in a proportion ranging from 0.1% to 8% by weight in relation to the total weight of the composition,
safrole in a proportion ranging from 0% to 5% by weight in relation to the total weight of the composition,
eugenol in a proportion ranging from 0% to 15% by weight in relation to the total weight of the composition.

29. Composition according to claim 28, wherein the linalool proportion ranges from 0.25% to 5% by weight in relation to the total weight of the composition.

* * * * *